United States Patent [19]

Gaffin

[11] Patent Number: 4,850,715

[45] Date of Patent: Jul. 25, 1989

[54] DUAL MATERIAL TEST SPECIMEN

[76] Inventor: Norman H. Gaffin, 704 Endicott Ave., Cinnaminson, N.J. 08077

[21] Appl. No.: 91,826

[22] Filed: Sep. 1, 1987

[51] Int. Cl.$^4$ .................. G01N 3/20; G01N 25/22
[52] U.S. Cl. .......................... 374/52; 374/55; 374/205; 428/616
[58] Field of Search ............ 374/45, 49, 50, 52, 374/46, 55, 187, 204; 335/215; 337/371; 428/616, 619

[56] References Cited

U.S. PATENT DOCUMENTS

| | | | |
|---|---|---|---|
| 2,130,829 | 9/1938 | Ackermann | 374/187 |
| 3,174,716 | 3/1965 | Salter | 374/49 X |
| 3,288,942 | 11/1966 | Voegeli | 335/215 X |
| 3,420,975 | 1/1969 | Thayer | 335/215 X |
| 3,504,282 | 3/1970 | Opsahl | 335/215 X |
| 3,828,606 | 8/1974 | Wolter | 374/45 |
| 3,922,903 | 12/1975 | Bornstein et al. | 374/50 |
| 4,217,398 | 8/1980 | Ty | 428/616 |
| 4,325,047 | 4/1982 | Inada et al. | 337/371 X |

Primary Examiner—Daniel M. Yasich
Attorney, Agent, or Firm—Paul & Paul

[57] ABSTRACT

A test specimen is provided, that is constructed of dual materials, which are preferably metallic materials and which are more preferably an austenitic iron alloy and a ferritic iron alloy. The specimen is generally constructed as a rectangular configuration, with two principal legs, connected together by substantially rigid connections at their ends, with the legs being of the different materials, such that, when the specimen is subjected to heat, one leg will expand linearly an amount greater than the other leg allowing the imposition of bending stress, whereby a given leg will experience both tension and compression. Observation may then be made, by a microscopic examination or otherwise, of those surfaces that are adjacent the portions of the legs that experience most of the tension and compression, such that the effects of temperature on the materials may be observed and recorded.

15 Claims, 1 Drawing Sheet

DUAL MATERIAL TEST SPECIMEN

SUMMARY OF THE INVENTION

A test specimen is provided for observing the effects of high temperature on specimens that have two components, with the components being of different materials, each having its own coefficient of thermal expansion. The structure is comprised of one leg of a first material, and another leg, eccentrically located relative to the first leg, so that the two legs are substantially parallel but spaced apart, but with substantially rigid connections between the legs, such that when one leg "grows", or expands linearally under elevated temperature conditions, it is constrained by the other eccentric leg which expands a lesser amount, thereby inducing compressive stresses on a generally concave side of the one leg and tensile stresses on the convex side of the one leg, with the other leg experiencing the converse on its different sides.

BACKGROUND OF THE INVENTION

It is known in the metallurgical testing art to employ dual alloy specimens for testing purposes. Such prior art specimens provide tensile stress, generally in a single alloy component only. For example, when the dual alloy comprises a austenitic material and a ferritic material, bonded side-by-side in some manner, as by welding or the like adjacent each other, this composite material, when subjected to the desired high temperature, will cause a parallel bending, such that the higher temperature coefficient material, namely the austenitic material, will experience only compressive stress, while the ferritic material will experience only tensile stress.

In accordance with such testing, the heat application is accomplished on a cyclic basis, and after a predetermined, desired number of heating cycles of the desired duration, the specimens are subjected to microscopic examination of the stressed surface areas, for damage.

Such testing is done in particular, in testing materials for thermal power plants, to determine likely damage at given life conditions, to use as a guide in replacement and repair of various boiler components or the like. This is because, upon repeatedly being subjected to high temperature conditions, cracks can form and gradually grow until failure occurs. The testing can be for making determinations of weld joints, or of making determinations of stress/strain of the base material structures themselves, whether they are steam pipes, pressure plates, valve components, or various other structures.

THE PRESENT INVENTION

The present invention is directed towards providing a dual alloy specimen which produces a bending stress in one of the alloys, and in the situation where the alloys are austenitic iron and ferritic iron, the bending stress will be produced in the austenitic alloy, by subjecting the specimen to heat in a furnace, carried to the desired temperature, for the desired period of time. A desired temperature may, for example, be 1050°F. The specimen may be carried to this temperature, for a predetermined period of time, for hundreds or even thousands of cycles, whereby visual observation may take place of the surfaces of the stressed portions of the legs of the specimen, generally at surfaces thereof, whereby crack formation or other changes in the portions of the legs near the surfaces may be observed. Such observations may be made by microscopic examination of outermost fiber surface portions, generally after a nondestructive polishing treatment is effected on the surfaces, to enhance the visual or microscopic examination.

In making such stress observations, it is possible with the present invention to induce tensile stresses in the austenitic alloy which cannot occur in specimens of prior art types.

It has been found that by thus constructing a specimen to effect bending stresses, it is possible to most closely approximate the actual operating conditions of boiler components that are subject to stresses, because there results both tensile and compressive stresses in each alloy of the specimen. That is, both tensile and compressive stresses may be observed and examined in each of the components of the specimen; whether they are the austenitic alloy component, the ferritic component alloy, or any other component.

Generally, the heating of the specimen occurs in an electric furnace. By using such a specimen that lends itself to such examination, is not necessary to employ artificial loading devices, such as mechanical loading devices, which may penetrate the furnace walls. Accordingly, more efficient testing is achieved.

Accordingly, it is a primary object of this invention to provide a novel test specimen for determining the results of cyclic heating of the specimen at high temperatures, particularly when the specimen is of multiple material construction.

It is a further object of the this invention to accomplish the above object wherein the specimen is constructed of two different metal alloys, and more specifically so, when one of the alloys is an austenitic iron alloy and where the other material is a ferritic iron alloy.

It is a further object of this invention to accomplish the above objects, wherein the specimen is constructed to have essentially two legs, one of a higher temperature coefficient of thermal expansion, and one of a lower temperature coefficient of thermal expansion, with the component of lower temperature coefficient of thermal expansion being eccentrically mounted relative to the higher temperature component, or in spaced-apart relation relative thereto, with the ends of the components being "tied" together, or rigidly connected to each other, such that a bowing or bending is effected in at least one, if not both, of the components, whereby tension and compression stresses may be observed and studied on at least one, it not both, of the components.

Other objects and advantages of the present invention will be readily apparent to those skilled in the art from a reading of the Brief Description of the Drawing Figures, the Detailed Description of the Preferred Embodiment, and the appended claims.

BRIEF DESCRIPTION OF THE DRAWING FIGURES

DETAILED DESCRIPTION OF THE PREFERRED EMBODIMENT

Figure 1:
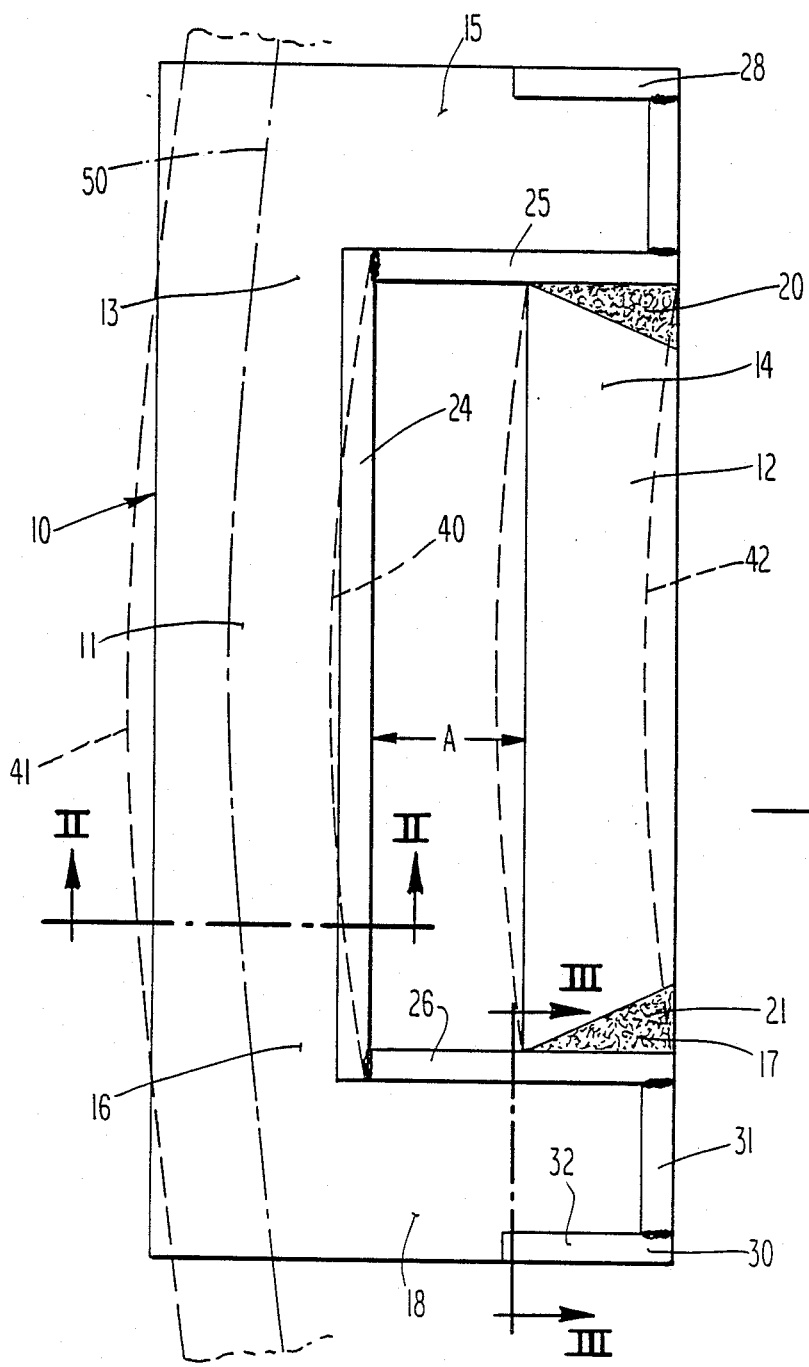
FIG. 1 is a side elevational view of the test specimen in accordance with this invention.

Referring now to the drawings in detail, reference is first made to FIG. 1, wherein the test specimen is generally designated by the numeral 10, as comprising a first leg 11 of a material having a higher temperature coefficient of thermal expansion, for example, an alloy of austenitic iron and a second leg 12 comprising a material of lower temperature coefficient of thermal expansion, which may, for example, be an alloy of ferritic iron. The legs 11 and 12 are connected at their respective upper ends 13 and 14 by generally rigid connecting means 15, and the lower ends 16 and 17 of the legs 11 and 12 are likewise connected by a rigid connected means 18, as indicated.

Preferably, the connecting means 15 and 18, and the leg 11 comprise a generally "C"-shaped structure as illustrated in FIG. 1, with the opening of the "C" being closed by the leg 12. The leg 12 is of generally rectangular cross-section, and is connected to the connecting portions 15 and 18 by suitable welds 20 and 21.

Figure 2:
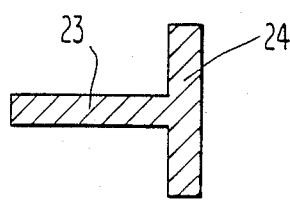
FIG. 2 is a sectional view taken through one leg of the test specimen of FIG. 1, generally along the line II—II of FIG. 1.
Figure 3:
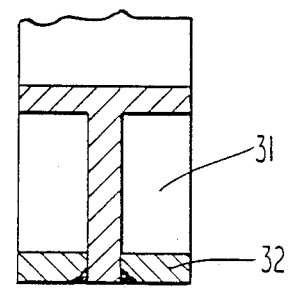
FIG. 3 is a fragmentary sectional view taken generally along the line III—III or the test specimen of FIG. 1.

The leg 11, as well as each of the end connections 18 and 15, are of generally "T"-shaped cross-section as illustrated in FIG. 2, and comprise a vertical component 23 for the "T", and a top or cross-bar component 24. The vertical component 23 may also be called a web component. It will be noted that the bar component 24 is on the inside of the specimen as viewed in FIG. 4, as are the similar components 25 and 26 of the connecting means 15 and 18, respectively.

The web component 23 faces outwardly on the leg 11, and upwardly and downwardly respectively, on the connection members 15 and 18.

"L"-shaped corners 28 and 30 are provided, two on the forward portion of the specimen as viewed in FIG. 1 and two on the opposite, or hidden side thereof, with each of the "L" corners comprising straight members such as 31, 32, welded together, and welded to the appropriate portion 25 or 26 of the "T"-shaped member, as well as being welded to appropriate webbed portions of the "T", not specifically illustrated in the drawings.

When the specimen 10 is subjected to high temperature, the leg 11, which may be of austenitic iron alloy construction, but which, in any event, will comprise the element with the higher temperature coefficient of thermal expansion, will expand more than the leg 12, which will be the leg of lower temperature coefficient of thermal expansion, and which may be of ferritic iron alloy construction, such that the leg 11 will bend to have a concave side 40 and a convex side 41. Similarly, leg 12 will bend to have a concave side 42 and a convex side 43, as such concave/convex sides are illustrated in phantom in FIG. 1.

By doing so, the convex side 41 of leg 11 will be bent, or stretched such that it is in tension, and the concave side 40 will be in compression. Similarly, the convex side 43 of leg 12 will be in tension and the concave side 41 will be in compression. This phenomenon results because the distance "A" between the legs 11 and 12, as indicated in FIG. 1, with the legs in spaced apart relation to each other, is an amount sufficient that, under the elevated temperature conditions, the growth of the legs 11 and 12 is sufficient that the leg 11 will grow enough to undergo such bending stresses, as will leg 12 also preferably grow to that extent, although a lesser amount than that of FIG. 11.

Each of the legs, it will be understood, has, at some location, a neutral axis 50 (although only one such axis is shown in FIG. 1), on one side of which the leg sees compressive stress and on the other side of which it sees tensile stress. The spacing "A" of components 12 and 11 is sometimes referred to as an "eccentric" mounting of the lower temperature component 12.

The extent to which such a specimen is stressed by a bending moment is a function of the magnitude of the bending moment and the section modulus. The section modulus is a known geometric characteristic of the cross-section of the member.

The resistance of a given cross-section of a member to bending is known as its Moment of Inertia(I). The Moment of Inertia results from the cross-sectional area and its distance from the neutral axis 50. The section modulus is the ratio of the distance (C) from the neutral axis to the Moment of Inertia(I). The stress (S) at any location "C" from the neutral axis is a function of the distance (C), Moment of Inertia(I), and the bending moment ($M_b$) as described in the following algebraic relationship:

$$S = M_b \times C/I$$

It will thus be seen that on the convex side 41 of component 11, the material at the maximum distance from the neutral axis 50 is being "pulled apart" by tensile stress. The area of the cross-section on the concave side 40 of number 11 is stressed in compression by the bending moment and is the maximum at the surface 40 which is the maximum distance from the neutral axis 50. Because the metallurgical changes that are caused by temperature are uniform in the specimen, the contribution of tensile stress to failure may be conclusively determined.

It will also be noted that the ratio of cross-sectional area of component 12 to component 11 should be inversely proportional to the ratio of the strength of the two materials at the desired test temperature. For example, in the specimen indicated, the austenitic material of leg 11 has the greatest strength at the higher test temperature; i.e., greater than the ferritic leg 12.

During the testing, the welded assembly is placed in an oven or furnace and heated to the desired temperature. This will provide the ability to observe, either visually, or microscopically, the combined affects of tensile stress and metallurgical changes that are induced at elevated temperature, without having to penetrate the walls of the test furnace with various loading or other stress-inducing devices.

It will also be apparent that the strain (measured deformation), in addition to cracks, voids or the like may be observed and measured by various techniques, during the testing that is done in accordance with this invention.

It will also be noted that if the distance "A" between the two legs, is two low, such that the two legs function almost as a bimetallic single leg, no bending moment will be produced, but the stress will actually be in shear.

As will be appreciated from the foregoing, there is the greatest visual and measureable stress at the side 41 of leg 11 in the test specimen, largely due to the fact that by using a specimen of "T"-shaped cross-section as indicated, for a given cross-sectional area, the greatest "stretching" will be at the convex side 41, as will the greatest strain exist along surface 41.

It will be seen, therefore, that the present invention provides the ability to put the austenitic material in tension at a predetermined level of stress, so that one can measure the strain and determine the effect of stress and strain on the microstructure, to make a determination as to longevity or long term life of the material. The longest term testing is desirable, because, as higher heats act upon the austenitic leg, the carbon in that leg is absorbed and causes a potential for weakening or a formation of cracks, because of the voids that are left due to the carbon absorption. In accordance with this invention, therefore, such metallurgical effects can be tested by the use of an efficient and readily manufactured specimen.

It will be apparent from the foregoing that various modifications may be made in the details of construction, as well as in the use and operation of a specimen in accordance with this invention, all within the scope of the invention as defined in the appended claims.

What is claimed is:

1. A test specimen for use in determining the results of high temperature on a specimen of dual component structures comprised of two materials having significant differences in their coefficients of thermal expansion, by examination of the specimen to determine the effects of stress, comprising:
    (a) a first leg of a material having a higher temperature coefficient of thermal expansion;
    (b) a second leg of a material having a lower temperature coefficient of thermal expansion;
    (c) said legs being disposed generally parallel to each other and each terminating in leg ends near and adjacent to each other;
    (d) connecting means rigidly connecting adjacent ends of the first and second legs together; and
    (e) with the legs being in spaced apart relation to each other.

2. The specimen of claim 1, wherein the spacing of the legs is an amount sufficient to, at elevated temperature conditions, where at least the first leg having the higher temperature coefficient of thermal expansion is subjected to bending stress, provide means for placing one side of the first leg in tension and the opposite, generally parallel, side of the first leg in compression.

3. The specimen of claim 2, wherein the first leg and said connecting means comprising a generally "C"-shaped structure of substantially the sam material.

4. The specimen of claim 2, wherein the first leg is of generally "T"-shaped cross-section, with the said one side of said first leg comprising the lower end of the vertical component of the "T".

5. The specimen of claim 2, wherein the second leg is of generally rectangular shaped cross-section.

6. The specimen of claim 3, wherein the first leg is of generally "T"-shaped cross-section, with the said one side of said first leg comprising the lower end of the vertical component of the "T".

7. The specimen of claim 3, wherein the first leg is of generally "T"-shaped cross-section, with the said one side of said first leg comprising the lower end of the vertical component of the "T" and wherein the second leg is of generally rectangular shaped cross-section.

8. The specimen of claim 4, wherein said connecting means are generally of "T"-shaped cross-section with the vertical components of the "T" facing away from each other.

9. The specimen of any one of claims 1-8, wherein said legs and connecting means are in welded connection as a one-piece specimen.

10. The specimen of any one of claims 1-9, wherein the legs are comprised of metals of different alloys.

11. The specimen of any one of claims 1-10, wherein the first leg is comprised of an austenitic iron alloy.

12. The specimen of any one of claims 1-9, wherein the second leg is comprised of a ferritic iron alloy.

13. The specimen of any one of claims 1-9, wherein the first leg is comprised of an austenitic iron alloy and the second leg is comprised of a ferritic iron alloy.

14. A test specimen for use in determining the results of high temperature on a specimen of dual component structures comprised of two material having significant differences in their coefficients of thermal expansion, by examination of the specimen to determine the effects of stress, comprising:
    (a) a first leg of a material having a higher temperature coefficient of thermal expansion;
    (b) a second leg of a material having a lower temperature coefficient of thermal expansion;
    (c) said legs being disposed generally parallel to each other and each terminating in leg ends near and adjacent to each other;
    (d) connecting means rigidly connecting adjacent ends of the first and second legs together; whereby stresses induced in the second leg by greater thermal expansion of the first leg have counterpart stresses imparted through the rigid connections to the first leg, and stresses induced in the first leg by lesser thermal expansion of the second leg have counterpart stresses imparted through the rigid connections to the second leg, upon subjecting the specimen to elevated temperature conditions; and
    (e) with the legs being in spaced apart relation to each other.

15. The specimen of claim 14, wherein the spacing of the legs is an amount sufficient to, at elevated temperature conditions, where at least the first leg having the higher temperature coefficient of thermal expansion is subjected to bending stress, provide means for placing one side of the first leg in tension and the opposite, generally parallel, side of the first leg in compression.

* * * * *